(12) United States Patent
Yamanaka et al.

(10) Patent No.: US 6,448,383 B2
(45) Date of Patent: Sep. 10, 2002

(54) METHOD FOR PRODUCING 1,2-NAPHTHOQUINONEDIAZIDE PHOTOSENSITIVE AGENT

(75) Inventors: Tomotaka Yamanaka, Chiba (JP); Masamichi Hayakawa, Chiba (JP)

(73) Assignee: Toyo Gosei Kogyo Co., Ltd., Chiba (JP)

( * ) Notice: Subject to any disclaimer, the term of this patent is extended or adjusted under 35 U.S.C. 154(b) by 0 days.

(21) Appl. No.: 09/851,008

(22) Filed: May 8, 2001

(30) Foreign Application Priority Data

May 8, 2000 (JP) ............................... 2000-134836

(51) Int. Cl.$^7$ ........................ C07C 303/28; G03F 7/022
(52) U.S. Cl. .................................................. 534/557
(58) Field of Search .......................................... 534/557

(56) References Cited

U.S. PATENT DOCUMENTS

| 4,957,846 A | * | 9/1990 | Jeffries, III et al. | ........ | 430/165 |
| 5,283,324 A | * | 2/1994 | Tomioka et al. | ............ | 534/557 |
| 5,618,932 A | * | 4/1997 | Zampini et al. | ............ | 534/557 |

FOREIGN PATENT DOCUMENTS

| JP | 3-48249 | 3/1991 |
| JP | 3-142468 | 3/1991 |
| JP | 3-158856 | 7/1991 |
| JP | 3-185447 | 8/1991 |
| JP | 3-215862 | 9/1991 |
| JP | 3-215863 | 9/1991 |
| JP | 4-29242 | 1/1992 |
| JP | 4-502519 | 5/1992 |
| JP | 4-282454 | 10/1992 |
| JP | 5-27428 | 2/1993 |
| JP | 5-27429 | 2/1993 |
| JP | 6-95374 | 4/1994 |
| JP | 6-167805 | 6/1994 |
| JP | 7-56331 | 3/1995 |
| JP | 7-104465 | 4/1995 |
| JP | 7-104467 | 4/1995 |
| JP | 7-159989 | 6/1995 |
| JP | 7-159990 | 6/1995 |
| JP | 7-168355 | 7/1995 |
| JP | 7-175213 | 7/1995 |
| JP | 7-219920 | 8/1995 |
| JP | 7-225476 | 8/1995 |
| JP | 7-230166 | 8/1995 |
| JP | 8-29978 | 2/1996 |
| JP | 8-202031 | 8/1996 |
| JP | 8-245461 | 9/1996 |
| JP | 8-320558 | 12/1996 |
| JP | 8-328247 | 12/1996 |

* cited by examiner

Primary Examiner—Fiona T. Powers
(74) Attorney, Agent, or Firm—Huntley & Associates

(57) ABSTRACT

A method for producing a high-purity 1,2-naphthoquinonediazide photosensitive agent containing a low level of impurities, by condensing, in an organic solvent other than amide, polyhydric phenolic compound and 1,2-naphthoquinonediazide-sulfonic acid halide in the presence of organic amine; subsequently adding amide solvent to the resultant reaction mixture; and separating the resulting organic amine acid salt through filtration.

12 Claims, No Drawings

METHOD FOR PRODUCING 1,2-NAPHTHOQUINONEDIAZIDE PHOTOSENSITIVE AGENT

BACKGROUND OF THE INVENTION

The present invention relates to a method for producing 1,2-naphthoquinonediazide photosensitive agent used in a positive-type photoresist.

Positive-type photo resists containing an alkali-soluble resin and a 1,2-naphthoquinonediazide photosensitive agent are materials known to have excellent resolution, sensitivity, and etching resistance, and are used for producing semiconductor elements and liquid crystal elements. Generally, the photosensitive agent used in such a positive-type photoresist can be obtained through esterification between a polyhydric phenolic compound having hydroxyl groups and a 1,2-naphthoquinonediazide-sulfonic acid halide. In recent years, miniaturization of semiconductor elements has imposed a requirement for a strict control of the level of impurities in photoresists. Accordingly, there is demand for reducing the impurity level of the 1,2-naphthoquinonediazide photosensitive agent used in the photoresists.

Japanese Patent Application Laid-Open (kokai) No. 8-328247 discloses one previous method for producing a 1,2-naphthoquinonediazide. There, polyhydric phenolic compound and a 1,2-naphthoquinonediazide-sulfonic acid halide are subjected to a condensation reaction in an organic solvent in the presence of an organic amine; the resultant reaction mixture is neutralized; the formed organic amine acid salt is filtered off; and the filtrate is poured into an aqueous acidic solution. However, this method results in the presence of organic amine, acid, or organic amine acid salt which cannot be removed to a satisfactory degree of purity.

A 1,2-naphthoquinonediazide photosensitive agent containing a low level of impurities may be obtained if the aforementioned condensation is performed in an amide solvent serving as a reaction solvent, then neutralizing the resultant reaction mixture, filtering off the formed organic amine acid salt, and pouring the filtrate into an aqueous acidic solution. However, this method is also deficient in that a 1,2-naphthoquinonediazide-sulfonic acid halide is decomposed in amide solvent, and the resulting 1,2-naphthoquinonediazide-sulfonic acid remains as an impurity in the resulting photosensitive agent product.

Accordingly, a continuing need exists for a process which provides 1,2-naphthoquinonediazide photosensitive agent containing very small amounts of impurities such as an organic amine, an acid, or acid salts of the organic amine, and 1,2-naphthoquinonediazide-sulfonic acid.

SUMMARY OF THE INVENTION

The present invention is based on the discovery that a high-purity 1,2-naphthoquinonediazide photosensitive agent containing a low level of impurities can be obtained by condensing, in an organic solvent other than amide, at least one polyhydric phenolic compound and at least one 1,2-naphthoquinonediazide-sulfonic acid halide in the presence of an organic amine; subsequently adding an amide solvent to the resultant reaction mixture; and filtering off the formed organic amine hydrohalide salt.

Accordingly, the present invention provides a method for producing 1,2-naphthoquinonediazide photosensitive agent, comprising condensing, in organic solvent other than amide, at least one polyhydric phenolic compound and at least one 1,2-napthoquinonediazide-sulfonic acid halide in the presence of organic amine; subsequently adding amide solvent to the resultant reaction mixture; and filtering off the formed organic amine acid salt.

In an alternative embodiment of the invention, there is provided a method for producing 1,2-naphthoquinonediazide photosensitive agent, comprising condensing, in organic solvent other than amide, at least one polyhydric phenolic compound and at least one 1,2-naphthoquinonediazide-sulfonic acid halide in the presence of organic amine; subsequently adding amide solvent to the resultant reaction mixture; further adding volatile acid so as to render the resultant reaction mixture acidic; and filtering off the formed organic amine acid salt.

In still another embodiment of the present invention, there is provided a method for producing 1,2-naphthoquinonediazide photosensitive agent, comprising condensing, in organic solvent other than amide, at least one polyhydric phenolic compound and at least one 1,2-naphthoquinonediazide-sulfonic acid halide in the presence of organic amine; subsequently adding amide solvent to the resultant reaction mixture; further adding volatile acid so as to render the resultant reaction mixture acidic; filtering off the formed organic amine acid salt; pouring the resultant filtrate into pure water or an aqueous solution of a volatile acid, to thereby form precipitates; and collecting the precipitates through filtration.

DETAILED DESCRIPTION OF THE INVENTION

According to the present invention, a 1,2-naphthoquinonediazide photosensitive agent can be obtained by condensing, in organic solvent other than amide, at least one polyhydric phenolic compound and at least one 1,2-naphthoquinonediazide-sulfonic acid halide in the presence of organic amine; subsequently adding amide solvent to the resultant reaction mixture; and filtering off the formed organic amine acid salt.

Representative polyhydric phenolic compounds which can be used in the instant process include benzophenones such as 2,3,4-trihydroxybenzophenone, 2,3,4,4'-tetrahydroxybenzophenone, 2,2',4,4'-tetrahydroxybenzophenone, 2,2',3,4,4'-pentahydroxybenzophenone, and 2,3,3',4,4'-pentahydroxybenzophenone; gallic acid alkyl esters; bis((poly)hydroxyphenyl)alkanes such as bis(4-hydroxy-2-methylphenyl)methane, bis(2,6-dimethyl-4-hydroxyphenyl)methane, 1,1-bis(4-hydroxyphenyl)cyclohexane, bis(2,4-dihydroxyphenyl)methane, 2,2-bis(2,4-dihydroxyphenyl)propane, bis (2,4-dimethyl-3-hydroxyphenyl)methane, (4-hydroxyphenyl)(2,3,4-hydroxyphenyl)methane, and 2-(4-hydroxyphenyl)-2-(2,3,4-hydroxyphenyl)propane; polyhydroxytriphenylalkanes disclosed, for example, in Japanese Patent Application Laid-Open (kokai) Nos. 3-142468, 3-158856, 4-29242, and 4-282454; polyhydroxybenzopyrans disclosed in Japanese Patent Application Laid-Open (kokai) No. 3-215863; polyhydroxyindanes disclosed, for example, in Japanese Patent Application Laid-Open (kokai) Nos. 3-215862 and 6-95374; polyhydroxycoumarones disclosed in Japanese Patent Application Laid-Open (kokai) Nos. 3-185447 and 7-56331; polyhydroxyphthalides disclosed in Japanese Patent Application Laid-Open (kokai) No. 5-27429; polyhydroxycoumarins disclosed in Japanese Patent Application Laid-Open (kokai) No. 5-27428; and polynuclear phenols disclosed, for example, in Japanese Patent Publication (kokoku) No. 4-502519 and Japanese Patent Application Laid-Open (kokai) Nos. 3-48249, 6-167805, 7-104465, 7-104467, 7-159989, 7-159990, 7-168355, 7-175213, 7-219920, 7-225476, 7-230166, 8-29978, 8-202031, 8-245461, and 8-320558. These polyhydric phenolic compounds can be used in reaction singly or in combination of two or more species.

Examples of 1,2-naphthoquinonediazide-sulfonic acid halides which can be used in the instant process include 1,2-naphthoquinonediazide-4-sulfonyl chloride, 1,2-naphthoquinonediazide-5-sulfonyl chloride, and 1,2-naphthoquinonediazide-6-sulfonyl chloride. These 1,2-naphthoquinonediazide-sulfonic acid halides can be used singly or in combination of two or more.

Examples of organic amines which can be used in the instant process include ethylamine, diethylamine, triethylamine, diisopropylamine, tripropylamine, triisobutylamine, triethanolamine, monomethyldicyclohexylamine, N-methylpiperidine, N-methylmorpholine, N-methylpyrrolidine, 1,4-dimethylpiperazine, pyridine, N,N-dimethylaniline, and N,N-dimethylaminopyridine. These amines can be used singly or in combination of two or more.

The reaction solvent used in the present invention is an organic solvent other than amide. Examples of preferred organic solvents include acetone, 1,4-dioxane, 1,3-dioxolane, tetrahydrofuran (THF), γ-butyrolactone, and propylene carbonate. These specific solvents are preferred. These solvents can be used singly or in combination of two or more.

After condensation is completed, amide solvent is added. Examples of preferred amide solvents which can be used include N-methylpyrrolidone, N,N-dimethylformamide, N,N-dimethylacetamide, and N,N-dimethylimidazolidinone, and at least one species selected therefrom is used. Especially preferred amide solvents which can be used include N-methylpyrrolidone, N,N-dimethylformamide, N,N-dimethylacetamide and N,N-dimethylimidazolidinone.

In a typical procedure, at least one polyhydric phenolic compound and at least one 1,2-naphthoquinonediazide-sulfonic acid halide are dissolved in solvent, and, to the resultant solution, organic amine or a solution of organic amine in solvent is added, to thereby effect a condensation reaction. Alternatively, polyhydric phenolic compound and organic amine can be dissolved in solvent, and, to the resultant solution, 1,2-naphthoquinonediazide-sulfonic acid halide or a solution of the halide in a solvent is added. Subsequently, the resultant mixture is allowed to react for about ten minutes to five hours with stirring. Combining the two solutions for effecting condensation is performed at the temperature range of about from −10° C. to 40° C., preferably at about 10–35° C., and condensation is carried out over a period of about from ten minutes to three hours.

The 1,2-naphthoquinonediazide-sulfonic acid halide is added in an amount of about 0.3–1.1 mol, preferably about 0.5–1.0 mol, based on 1 equivalent, in terms of hydroxyl group, of the polyhydric phenolic compound. When the amount is less than about 0.3 mol, the photoresist formed from an alkali-soluble resin exhibits poor contrast, whereas when the amount is greater than about 1.2 mol, unreacted 1,2-naphthoquinonediazide-sulfonic acid halide is prone to remain. The organic amine is added typically in an amount of about 1.0–1.5 mol, preferably about 1.05–1.2 mol based on 1 mol of the 1,2-naphthoquinonediazide-sulfonic acid halide. When the amount is less than about 1.0 mol, 1,2-naphthoquinonediazide-sulfonic acid halide is prone to remain, whereas when the amount is in excess of about 1.5 mol, a 1,2-quinonediazide moiety is readily decomposed by an excessive organic amine. The solvent is used in an amount equal to about 2–10 times, preferably about 3–5 times, the total weight of the 1,2-naphthoquinonediazide-sulfonic acid halide and the polyhydric phenolic compound. When the amount is less than about 2 times the total weight, dissolution of a reaction component might be incomplete, and storage stability, good storage stability being one object of the present invention, becomes poor. When the amount of in excess of about 10 times the total weight, a large amount of water is required to cause re-precipitation, which is economically disadvantageous.

After condensation is complete, amide solvent is added. The amide solvent is used in an amount by weight preferably about 0.2–2 times, more preferably about 0.25–1 times, the weight of the solvent employed for condensation. When the amount is less than about 0.2 times the weight, sufficient effects of the present invention cannot be attained, whereas when the amount is about 2 times or more the weight, a large amount of water is required to cause re-precipitation, which is economically disadvantageous.

After addition of the amide solvent to the reaction mixture is complete, the resulting organic amine acid salt is separated off through filtration. Preferably, the reaction mixture is rendered acidic by adding a volatile acid prior to filtration and subsequently separating off the formed organic amine acid salt through filtration. Examples of volatile acid which can be so used in acidification include hydrochloric acid, acetic acid, and formic acid. The volatile acid is added in an amount, represented by the ratio of (1,2-naphthoquinonediazide-sulfonic acid halide/mol+acid to be added/mol) to (organic amine/mol), of about 1.0–1.5, preferably about 1.02–1.15.

After removal of the organic amine acid salt through filtration, the reaction mixture is poured into pure water or an aqueous solution of a volatile acid, to thereby re-precipitate a 1,2-naphthoquinonediazide photosensitive agent. The re-precipitated 1,2-naphthoquinonediazide photosensitive agent is then filtered off, washed with pure water or a diluted aqueous solution of acid, and dried, to thereby yield the desired 1,2-naphthoquinonediazide photosensitive agent. In a typical procedure, the reaction mixture is poured into pure water, to thereby re-precipitate the photosensitive agent, and the re-precipitated 1,2-naphthoquinonediazide photosensitive agent is separated through filtration. However, pouring the reaction mixture into an aqueous acidic solution is preferred so as to facilitate filtration, since use of pure water might make filtration difficult. Examples of preferred acids to render the reaction mixture weakly acidic include volatile acids such as hydrochloric acid, acetic acid, and formic acid. The diluted aqueous acidic solution has an acid concentration of approximately 0.02–0.5 N. The amount of pure water or the aqueous acidic solution used for re-precipitation is about 2–10 times the weight of the organic solvent used, preferably about 3–6 times. The re-precipitated photosensitive agent is separated through filtration, washed with pure water or a diluted aqueous acidic solution, and dried in vacuum, to thereby remove the volatile acid.

The present invention is still more fully described in the following examples, which are representative and should not be construed as limiting the invention.

EXAMPLES

Example 1

Comparative Production Example 1

Into a three-neck flask, 2,3,4,4'-tetrahydroxybenzophenone (31 g), 1,2- naphthoquinonediazide-5-sulfonyl chloride (85.5 g), and tetrahydroifuran (570 g) were placed, and the resultant mixture was dissolved, to thereby provide a homogeneous solution. Subsequently, a mixture of triethylamine/tetrahydrofuran (35.4 g/35.4 g) was added dropwise to the solution at 30–35° C. over one hour. Thirty minutes after completion of addition, 35% hydrochloric acid (6.6 g) was added dropwise to the resultant mixture. The formed triethylamine hydrochloride was separated off through filtration. The resultant filtrate was poured into a 0.1% aqueous hydrochloric acid solution (3,000 ml) maintained at 30–35° C. The formed precipitates were collected through filtration, washed with water, and dried at 45° C., to thereby yield 100 g of a 2,3,4,4'-tetrahydroxybenzophenone 1,2-naphthoquinonediazide-5-sulfonate ester.

Production Example 1

Into a three-neck flask, 2,3,4,4'-tetrahydroxybenzophenone (31 g), 1,2-naphthoquinonediazide-5-sulfonyl chloride (85.5 g), and tetrahydrofuran (450 g) were placed, and the resultant mixture was dissolved, to thereby provide a homogeneous solution. Subsequently, a mixture of triethylamine/tetrahydrofuran (35.4 g/35.4 g) was added dropwise to the solution at 30–35° C. over one hour. Thirty minutes after completion of addition, N,N'-dimethylacetamide (100 g) was added to the resultant mixture. Further, 30 minutes after addition of the amide was complete, 35% hydrochloric acid (6.6 g) was added dropwise to the resultant mixture. The formed triethylamine hydrochloride was separated off through filtration. The resultant filtrate was poured into a 0.1% aqueous hydrochloric acid solution (2,800 ml) maintained at 20–25° C. The formed precipitates were collected through filtration, washed with water, and dried at 45° C., to thereby yield 100 g of a 2,3,4,4'-tetrahydroxybenzophenone 1,2-naphthoquinonediazide-5-sulfonate ester.

The chloride ion content of the photosensitive agent obtained in Comparative Production Example 1 and that obtained in Production Example 1 were measured. As shown in Table 1, the chloride ion content of the photosensitive agent obtained in Production Example 1 according to the present invention is remarkably low.

TABLE 1

|  | Chloride ion content |
|---|---|
| Comparative Production Example 1 | 230 ppm |
| Production Example 1 | ≦10 ppm |

Example 2

Comparative Production Example 2

Into a three-neck flask, 2,3,4,4'-tetrahydroxybenzophenone (29 g), 1,2-naphthoquinonediazide-5-sulfonyl chloride (95 g), and 1,3-dioxolane (600 g) were placed, and the resultant mixture was dissolved, to thereby prepare a homogeneous solution. Subsequently, a mixture of triethylamine/dioxane (39.4 g/39.4 g) was added dropwise to the solution at 30–35° C. over one hour. Thirty minutes after completion of addition, 35% hydrochloric acid (7.4 g) was added dropwise to the resultant mixture. The formed triethylamine hydrochloride was separated off through filtration. The resultant filtrate was poured into a 0.1% aqueous hydrochloric acid solution (3,000 ml) maintained at 30–35° C. The formed precipitates were collected through filtration, washed with water, and dried at 45° C., to thereby yield 100 g of a 2,3,4,4'-tetrahydroxybenzophenone 1,2-naphthoquinonediazide-5-sulfonate ester.

Production Example 2

Into a three-neck flask, 2,3,4,4'-tetrahydroxybenzophenone (29 g), 1,2-naphthoquinonediazide-5-sulfonyl chloride (95 g), and 1,3-dioxolane (400 g) were placed, and the resultant mixture was dissolved, to thereby prepare a homogeneous solution. Subsequently, a mixture of triethylamine/1,3-dioxolane (39.4 g/39.4 g) was added dropwise to the solution at 30–35° C. over one hour. Thirty minutes after completion of addition, N-methylpyrrolidone (100 g) was added to the resultant mixture. Further, 30 minutes after addition of N-methylpyrrolidone, 35% hydrochloric acid (7.4 g) was added dropwise to the mixture. The formed triethylamine hydrochloride was separated off through filtration. The resultant filtrate was poured into a 0.1% aqueous hydrochloric acid solution (2,800 ml) maintained at 20–25° C. The formed precipitates were collected through filtration, washed with water, and dried at 45° C., to thereby yield 100 g of a 2,3,4,4'-tetrahydroxybenzophenone 1,2-naphthoquinonediazide-5-sulfonate ester.

The chloride ion content of the photosensitive agent obtained in Comparative Production Example 2 and that obtained in Production Example 2 were measured. As shown in Table 2, the chloride ion content of the photosensitive agent obtained in Production Example 2 according to the present invention is remarkably low.

TABLE 2

|  | Chloride ion content |
|---|---|
| Comparative Production Example 2 | 270 ppm |
| Production Example 2 | 15 ppm |

Example 3

Comparative Production Example 3

Into a three-neck flask, 2,3,4-trihydroxybenzophenone (35 g), 1,2-naphthoquinonediazide-5-sulfonyl chloride (81.4 g), and acetone (600 g) were placed, and the resultant mixture was dissolved, to thereby prepare a homogeneous solution. Subsequently, triethylamine (33.7 g) was added dropwise to the solution at 30–35° C. over one hour. Thirty minutes after completion of addition, 35% hydrochloric acid (6.3 g) was added dropwise to the solution. The formed triethylamine hydrochloride was separated through filtration. The resultant filtrate was poured into a 0.1% aqueous hydrochloric acid solution (1,800 ml) maintained at 30–35° C. The formed precipitates were collected through filtration, washed with water, and dried at 45° C., to thereby yield 100 g of a 2,3,4-trihydroxybenzophenone 1,2-naphthoquinonediazide-5-sulfonate ester.

Production Example 3

Into a three-neck flask, 2,3,4-trihydroxybenzophenone (35 g), 1,2-naphthoquinonediazide-5-sulfonyl chloride (81.4 g), and acetone (400 g) were placed, and the resultant mixture was dissolved, to thereby prepare a homogeneous solution. Subsequently, triethylamine (33.7 g) was added dropwise to the solution at 30–35° C. over one hour. Thirty minutes after completion of addition, N,N-dimethylformamide (100 g) was added to the solution. Further, 30 minutes after addition of N,N-dimethylformamide, 35% hydrochloric acid (6.3 g) was added dropwise to the mixture. The formed triethylamine hydrochloride was separated off through filtration. The resultant filtrate was poured into a 0.1% aqueous hydrochloric acid solution (1,700 ml) maintained at 20–25° C. The formed precipitates were collected through filtration, washed with water, and dried at 45° C., to thereby yield 100 g of a 2,3,4-trihydroxybenzophenone 1,2-naphthoquinonediazide-5-sulfonate ester.

The chloride ion content of the photosensitive agent obtained in Comparative Production Example 3 and that obtained in Production Example 3 were measured. As shown in Table 3, the chloride ion content of the photosensitive agent obtained in Production Example 3 according to the present invention is remarkably low.

TABLE 3

|  | Chloride ion content |
|---|---|
| Comparative Production Example 3 | 130 ppm |
| Production Example 3 | 10 ppm |

Example 4

Comparative Production Example 4

Into a three-neck flask, 3,3'-bis(2-hydroxy-5-methylbenzyl)-2,2'-dihydroxy-5,5'-dimethyldiphenylmethane (47.0 g), 1,2-naphthoquinonediazide-5-sulfonyl chloride (67.4 g), and acetone (800 g) were placed, and the resultant mixture was dissolved, to thereby prepare a homogeneous solution. Subsequently, a mixture of triethylamine/acetone (27.9 g/27.9 g) was added dropwise to the solution at 30–35° C. over one hour. Thirty minutes after completion of addition, 35% hydrochloric acid (5.2 g) was added dropwise to the resultant mixture. The formed triethylamine hydrochloride was separated through filtration. The resultant filtrate was poured into a 0.1% aqueous hydrochloric acid solution (2,700 ml) maintained at 20–25° C. The formed precipitates were collected through filtration, washed with water, and dried at 45° C., to thereby yield 100 g of a 3,3'-bis(2-hydroxy-5-methylbenzyl)-2,2'-dihydroxy-5,5'-dimethyldiphenylmethane 1,2-naphthoquinonediazide-5-sulfonate ester.

Production Example 4

Into a three-neck flask, 3,3'-bis(2-hydroxy-5-methylbenzyl)-2,2'-dihydroxy-5,5'-dimethyldiphenylmethane (47.0 g), 1,2-naphthoquinonediazide-5-sulfonyl chloride (67.4 g), and acetone (550 g) were placed, and the resultant mixture was dissolved, to thereby prepare a homogeneous solution. Subsequently, a mixture of triethylamine/acetone (27.9 g/27.9 g) was added dropwise to the solution at 30–35° C. over one hour. Thirty minutes after completion of addition, N-methylpyrrolidone (150 g) was added to the resultant mixture. Further, 30 minutes after addition of N-methylpyrrolidone was complete, 35% hydrochloric acid (5.2 g) was added dropwise to the resultant mixture. The formed triethylamine hydrochloride was separated off through filtration, and the resultant filtrate was poured into a 0.1% aqueous hydrochloric acid solution (2,500 ml) maintained at 20–25° C. The formed precipitates were collected through filtration, washed with water, and dried at 45° C., to thereby yield 100 g of a 3,3'-bis(2-hydroxy-5-methylbenzyl)-2,2'-dihydroxy-5,5'-dimethyldiphenylmethane 1,2-naphthoquinonediazide-5-sulfonate ester.

The chloride ion content of the photosensitive agent obtained in Comparative Production Example 4 and that obtained in Production Example 4 were measured. As shown in Table 4, the chloride ion content of the photosensitive agent obtained in Production Example 4 according to the present invention is remarkably low.

TABLE 4

|  | Chloride ion content |
|---|---|
| Comparative Production Example 4 | 185 ppm |
| Production Example 4 | 20 ppm |

Example 5

Comparative Production Example 5

Into a three-neck flask, 2,3,4-trihydroxybenzophenone (35 g), 1,2-naphthoquinonediazide-5-sulfonyl chloride (81.4 g), acetone (400 g), and N-methylpyrrolidone (100 g) were placed, and the resultant mixture was dissolved, to thereby prepare a homogeneous solution. Subsequently, triethylamine (33.7 g) was added dropwise to the solution at 30–35° C. over one hour. Thirty minutes after completion of addition, 35% hydrochloric acid (6.3 g) was added dropwise to the resultant mixture. The formed triethylamine hydrochloride was separated through filtration. The resultant filtrate was poured into a 0.1% aqueous hydrochloric acid solution (1,700 ml) maintained at 20–25° C. The formed precipitates were collected through filtration, washed with water, and dried at 45° C., to thereby yield 100 g of a 2,3,4-trihydroxybenzophenone 1,2-naphthoquinonediazide-5-sulfonate ester.

Production Example 5

Into a three-neck flask, 2,3,4-trihydroxybenzophenone (35 g), 1,2-naphthoquinonediazide-5-sulfonyl chloride (81.4 g), and acetone (400 g) were placed, and the resultant mixture was dissolved, to thereby prepare a homogeneous solution. Subsequently, triethylamine (33.7 g) was added dropwise to the solution at 30–35° C. over one hour. Thirty minutes after completion of addition, N-methylpyrrolidone (100 g) was added to the resultant mixture. Further, 30 minutes after addition of N-methylpyrrolidone was complete, 35% hydrochloric acid (6.3 g) was added dropwise to the resultant mixture. The formed triethylamine hydrochloride was separated off through filtration. The resultant filtrate was poured into a 0.1% aqueous hydrochloric acid solution (1,700 ml) maintained at 20–25° C. The formed precipitates were collected through filtration, washed with water, and dried at 45° C., to thereby yield 100 g of a 2,3,4-trihydroxybenzophenone 1,2-naphthoquinonediazide-5-sulfonate ester.

The sulfonate ion content of the photosensitive agent obtained in Comparative Production Example 5 and that obtained in Production Example 5 were measured. As shown in Table 5, the sulfonate ion content of the photosensitive agent obtained in the case in which the amide solvent was added after completion of condensation is remarkably low.

TABLE 5

| | Sulfonate ion content |
|---|---|
| Comparative Production Example 5 | 140 ppm |
| Production Example 5 | 25 ppm |

As described hereinabove, according to the present invention, a high-purity 1,2-naphthoquinonediazide photosensitive agent containing a low level of impurities can be produced by effecting condensation, in an organic solvent other than amide, between a polyhydric phenolic compound and a 1,2-naphthoquinonediazide-sulfonic acid halide in the presence of an organic amine; subsequently adding an amide solvent to the resultant reaction mixture; and separating off the formed organic amine hydrohalide salt through filtration.

We claim:

1. A method for producing 1,2-naphthoquinonediazide photosensitive agent, comprising condensing, in organic solvent other than amide, at least one polyhydric phenolic compound and at least one 1,2-naphthoquinonediazide-sulfonic acid halide in the presence of organic amine; subsequently adding amide solvent to the resultant reaction mixture; and filtering off the formed organic amine acid salt.

2. A method for producing 1,2-naphthoquinonediazide photosensitive agent, comprising condensing, in organic solvent other than amide, at least one polyhydric phenolic compound and at least one 1,2-naphthoquinonediazide-sulfonic acid halide in the presence of organic amine; subsequently adding amide solvent to the resultant reaction mixture; further adding volatile acid so as to render the resultant reaction mixture acidic; and filtering off the resulting organic amine acid salt.

3. A method for producing 1,2-naphthoquinonediazide photosensitive agent, comprising condensing, in organic solvent other than amide, at least one polyhydric phenolic compound and at least one 1,2-naphthoquinonediazide-sulfonic acid halide in the presence of organic amine; subsequently adding amide solvent to the resultant reaction mixture; further adding volatile acid so as to render the resultant reaction mixture acidic; filtering off the resulting organic amine acid salt; pouring the resultant filtrate into pure water or an aqueous solution of a volatile acid, to thereby form precipitates; and collecting the precipitates through filtration.

4. A method for producing a 1,2-naphthoquinonediazide photosensitive agent according to claim 1, wherein the amide solvent is at least one amide selected from N-methylpyrrolidone, N,N-dimethylformamide, N,N-dimethylacetamide, and N,N-dimethylimidazolidinone.

5. A method for producing a 1,2-naphthoquinonediazide photosensitive agent according to claim 2, wherein the amide solvent is at least one amide selected from N-methylpyrrolidone, N,N-dimethylformamide, N,N-dimethylacetamide, and N,N-dimethylimidazolidinone.

6. A method for producing a 1,2-naphthoquinonediazide photosensitive agent according to claim 3, wherein the amide solvent is at least one amide selected from N-methylpyrrolidone, N,N-dimethylformamide, N,N-dimethylacetamide, and N,N-dimethylimidazolidinone.

7. A method for producing a 1,2-naphthoquinonediazide photosensitive agent according to claim 1, wherein the organic solvent used in the condensation step is at least one selected from acetone, 1,4-dioxane, 1,3-dioxolane, THF, γ-butyrolactone, and propylene carbonate.

8. A method for producing a 1,2-naphthoquinonediazide photosensitive agent according to claim 2, wherein the organic solvent used in the condensation step is at least one selected from acetone, 1,4-dioxane, 1,3-dioxolane, THF, γ-butyrolactone, and propylene carbonate.

9. A method for producing a 1,2-naphthoquinonediazide photosensitive agent according to claim 3, wherein the organic solvent used in the condensation step is at least one selected from acetone, 1,4-dioxane, 1,3-dioxolane, THF, γ-butyrolactone, and propylene carbonate.

10. A method for producing a 1,2-naphthoquinonediazide photosensitive agent according to claim 4, wherein the organic solvent used in the condensation step is at least one selected from acetone, 1,4-dioxane, 1,3-dioxolane, THF, γ-butyrolactone, and propylene carbonate.

11. A method for producing a 1,2-naphthoquinonediazide photosensitive agent according to claim 5, wherein the organic solvent used in the condensation step is at least one selected from acetone, 1,4-dioxane, 1,3-dioxolane, THF, γ-butyrolactone, and propylene carbonate.

12. A method for producing a 1,2-naphthoquinonediazide photosensitive agent according to claim 6, wherein the organic solvent used in the condensation step is at least one selected from acetone, 1,4-dioxane, 1,3-dioxolane, THF, γ-butyrolactone, and propylene carbonate.

* * * * *